US009327078B2

(12) United States Patent
Slate et al.

(10) Patent No.: US 9,327,078 B2
(45) Date of Patent: *May 3, 2016

(54) DEVICE AND METHOD FOR THE AUTOMATIC INITIATION OF AN INJECTION

(71) Applicant: Avant Medical Corp., Thousands Oaks, CA (US)

(72) Inventors: John B. Slate, Encinitas, CA (US); Michael W. Burk, San Marcos, CA (US)

(73) Assignee: AVANT MEDICAL CORPORATION, Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/655,280

(22) Filed: Oct. 18, 2012

(65) Prior Publication Data

US 2013/0046277 A1 Feb. 21, 2013

Related U.S. Application Data

(63) Continuation of application No. 13/198,561, filed on Aug. 4, 2011, now Pat. No. 8,292,843, which is a continuation of application No. 11/855,018, filed on Sep. 13, 2007, now Pat. No. 8,012,120.

(51) Int. Cl.
*A61M 5/42* (2006.01)
*A61M 5/20* (2006.01)
*A61M 5/30* (2006.01)

(52) U.S. Cl.
CPC . *A61M 5/20* (2013.01); *A61M 5/30* (2013.01); *A61M 5/425* (2013.01); *A61M 2005/2073* (2013.01); *A61M 2205/13* (2013.01)

(58) Field of Classification Search
CPC ..... A61M 5/20; A61M 5/30; A61M 2205/13; A61M 2005/2073; A61M 5/425
USPC ....................................................... 604/65–68
See application file for complete search history.

(56) References Cited

U.S. PATENT DOCUMENTS

| 4,006,736 | A | * | 2/1977 | Kranys et al. ................. 600/432 |
|---|---|---|---|---|
| 4,080,966 | A | | 3/1978 | McNally et al. |
| 4,457,751 | A | | 7/1984 | Rodler |
| 4,551,133 | A | | 11/1985 | Zegers de Beyl et al. |
| 4,752,289 | A | | 6/1988 | Balding et al. |
| 4,998,914 | A | | 3/1991 | Wiest et al. |
| 5,078,682 | A | | 1/1992 | Miki et al. |

(Continued)

*Primary Examiner* — Nicholas Lucchesi
*Assistant Examiner* — Melissa A Snyder
(74) *Attorney, Agent, or Firm* — Sarah Rouse Janosik

(57) ABSTRACT

A system and method to automatically initiate an injection procedure of a medicament into a patient. In the system, a delivery assembly includes an injector for infusing the medicament into the patient. Further, the system includes a monitor for detecting a parameter characteristic of the procedure, for instance, a pressure indicative of a partial vacuum between the injector and the injection site, a pressure exerted by the patient against the delivery assembly, a conductance, a capacitance, or an optical blood reading. Also, the system includes a timer for determining compliance of the parameter within a predetermined range during a first time interval. In response to the timer, an actuator initiates the injection procedure at the expiration of the first time interval. Further, the actuator may stop the injection procedure if the parameter is outside the predetermined range during a second time interval.

20 Claims, 3 Drawing Sheets

(56) References Cited

U.S. PATENT DOCUMENTS

| | | |
|---|---|---|
| 5,114,406 A | 5/1992 | Gabriel et al. |
| 5,141,496 A | 8/1992 | Dalto et al. |
| 5,425,715 A | 6/1995 | Dalling et al. |
| 5,514,097 A | 5/1996 | Knauer |
| 5,637,094 A | 6/1997 | Stewart, Jr. et al. |
| 5,840,026 A * | 11/1998 | Uber et al. .................... 600/431 |
| 6,077,247 A | 6/2000 | Marshall et al. |
| 6,099,503 A | 8/2000 | Stradella |
| 6,149,626 A | 11/2000 | Bachynsky et al. |
| 6,203,530 B1 | 3/2001 | Stewart, Sr. |
| 6,224,567 B1 | 5/2001 | Roser |
| 6,280,421 B1 | 8/2001 | Kirchhofer et al. |
| 6,406,456 B1 * | 6/2002 | Slate et al. ..................... 604/68 |
| 6,485,465 B2 | 11/2002 | Moberg et al. |
| 6,620,133 B1 | 9/2003 | Steck |
| 6,817,986 B2 | 11/2004 | Slate et al. |
| 6,890,319 B1 | 5/2005 | Crocker |
| 8,012,120 B2 | 9/2011 | Slate et al. |
| 8,292,843 B2 | 10/2012 | Slate et al. |
| 2002/0173769 A1 | 11/2002 | Gray et al. |

* cited by examiner

DEVICE AND METHOD FOR THE AUTOMATIC INITIATION OF AN INJECTION

This application is a continuation of application Ser. No. 13/198,561, filed Aug. 4, 2011, which is currently and which is a continuation of application Ser. No. 11/855,018, filed Sep. 13, 2007, now U.S. Pat. No. 8,012,120. The contents of application Ser. Nos. 13/198,561 and 11/855,018 are incorporated herein by reference.

FIELD OF THE INVENTION

The present invention pertains generally to systems and methods for injecting fluid medicaments into the body of a patient. More particularly, the present invention pertains to injectors that can be used by a patient to self-administer a fluid medicament. The present invention is particularly, but not exclusively, useful as a system and method for ensuring proper conditions to prevent premature injections and to prevent the continuation of improper injections.

BACKGROUND OF THE INVENTION

As medical technology advances, increasing numbers of patients are able to live with chronic conditions. Often, these patients are required to self-administer the necessary medications. In certain cases, the chronic conditions may require self-injection of one or more medications on a regular basis. Diabetes, for instance, is a common disease which requires sufferers to inject themselves with insulin one or more times each day.

Generally, self-administered injections are of the subcutaneous type. Subcutaneous injections are provided into the tissue just under the skin in order to provide a slower release of a medicinal substance into the body and thus guard against over-reaction in other portions of the body. Typically subcutaneous injections are performed into the fascia and fat tissue just under the skin.

When medical personnel perform a subcutaneous injection on patients, they usually pucker the flesh prior to applying the injection. As a result, the skin and its associated underlying structures, including a subcutaneous adipose tissue, are essentially isolated. Further, puckering the flesh firms the surface fascia to facilitate insertion of the medicament. While it is not difficult for a medical person to perform a subcutaneous injection in this manner, a self-injection into a patient's arm, back of arm, or buttocks cannot be preformed with the flesh puckering technique.

To overcome this limitation, a number of injection devices have been designed specifically for self-injections. Such devices may utilize a vacuum or other structure to properly prepare the patient's flesh for an injection. While these devices make self-injections into difficult-to-reach injection sites possible, it still can be difficult to correctly administer the required injection every time. Specifically, it can be difficult for a patient to determine when the injection site is ready for an injection and to avoid premature injections. Also, it can be difficult for a patient to ensure that injection conditions are maintained throughout the injection so that the injection is effective.

In light of the above, it is an object of the present invention to provide a system and method for performing injections that is convenient to use and that requires minimal manipulation before, during, and after an injection. Another object of the present invention is to provide a system and method for automatically initiating an injection procedure when predetermined injection conditions are met for a predetermined period of time. Another object of the present invention is to provide a system and method for automatically stopping the injection procedure when it is determined that injection conditions are no longer met. Still another object of the present invention is to provide a system and method for successfully performing self-injections with the use of only one hand. Another object of the present invention is to provide a system and method for performing injections that is easy to use, is relatively simple to manufacture, and is comparatively cost effective.

SUMMARY OF THE INVENTION

The present invention is directed to a system and method for automatically initiating and stopping a procedure for injecting a fluid medicament into a patient. As a result, the system assures that difficult injections, such as self-injections in difficult-to-reach areas of the body, are performed only when preferred injection conditions are observed. For purposes of the present invention, the system includes a fluid delivery assembly that includes an injector that infuses a predetermined volume of the medicament into the patient. Structurally, the fluid delivery assembly includes a fluid chamber that holds the fluid medicament in fluid communication with the injector. In the fluid delivery assembly, a plunger is positioned in the fluid chamber for advancement through the chamber to expel fluid through the injector. Also, a drive mechanism is provided for advancing the plunger through the chamber.

In addition to the fluid delivery assembly, the system includes a monitor for detecting an operational parameter characteristic of the procedure. Specifically, the operational parameter detected by the monitor may be a pressure that is indicative of a partial vacuum established between the injector and an injection site on the patient. It may also be a reaction pressure exerted by the patient against the fluid delivery assembly, a conductance, a capacitance, or an optical blood reading.

Also, the system is equipped with a timer that is electronically connected to the monitor to observe the operational parameter during contiguous first and second time periods. With this connection, the timer may determine whether the operational parameter stays within a predetermined range throughout the first time interval and the second time interval. Further, the timer communicates with an actuator that is connected to the fluid delivery assembly. For purposes of the present invention, the actuator is able to selectively initiate and stop the injection procedure performed by the fluid delivery assembly.

In operation, the injector of the fluid delivery assembly is positioned at the injection site. Thereafter, the monitor detects the operational parameter. As soon as the monitor has detected that the operational parameter has successfully stayed within the predetermined range for the first time interval, the monitor alerts the actuator. In response, the actuator initiates the injection procedure by the fluid delivery assembly. For the present invention, the length of time required for the injection procedure coincides with the second time interval. Therefore, if the monitor determines that the operational parameter falls outside the predetermined range during the second time interval, the monitor alerts the actuator and the actuator stops the injection procedure. In this manner, the system ensures that effective injections are administered and that non-effective injections are aborted.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
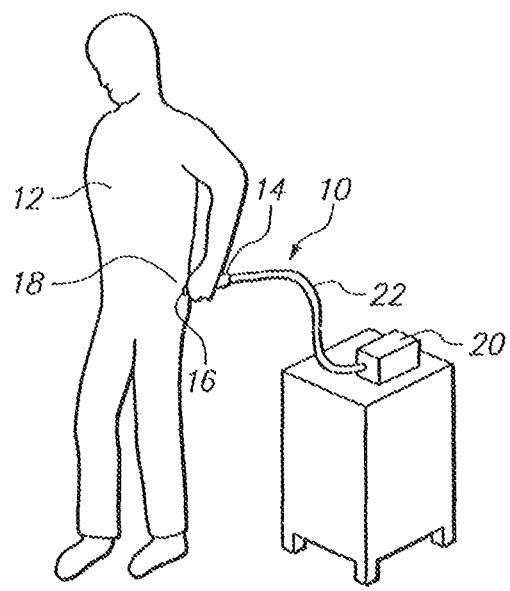
FIG. 1 is a perspective view of a patient performing a self-injection in accordance with the present invention.

Referring initially to FIG. 1, a system for automatically initiating an injection procedure to deliver a fluid medicament in accordance with the present invention is shown and is generally designated 10. For the purposes of the present invention, the system 10 is used to deliver a fluid medicament to a patient 12 by selectively injecting the fluid medicament either into a muscle (intra-muscular), subcutaneous, or into the skin (intra-dermal). For all modes of operation, the system 10 essentially includes a housing 14 that contains a fluid delivery assembly 16 and components for monitoring and automatically acting on operational parameters as discussed below. To stabilize and hold the fluid delivery assembly 16 against the skin 18 of the patient 12 during an injection, the system 10 may include a suction pump 20 which may be integrated into housing 14 and connected in fluid communication with the fluid delivery assembly 16 via a vacuum line 22. More specifically, the generation of a partial vacuum between the fluid delivery assembly 16 and the skin 18 of the patient 12 accomplishes at least three functions. First, the partial vacuum forms the skin 18 with a desired tension for the injection. It should be noted that the desired tension for an intra-muscular injection is different than the tension for an intra-dermal injection. Second, as stated above, the partial vacuum helps stabilize and hold the fluid delivery assembly 16 against the patient 12. And third, the partial vacuum generates a fluid seal between the fluid delivery assembly 16 and the patient 12 that allows for the effective delivery or injection of a fluid medicament.

Figure 2:
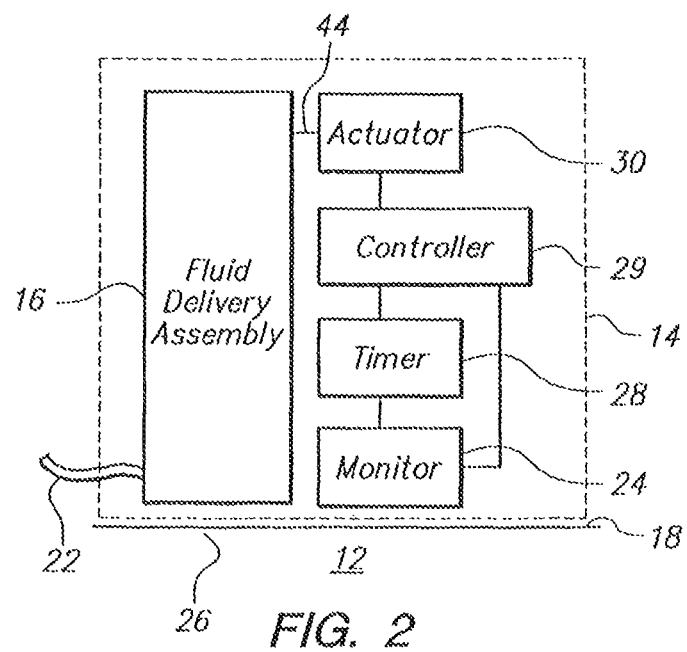
FIG. 2 is a schematic diagram of the operational components of the fluid delivery assembly of the present invention.

Referring now to FIG. 2, the system 10 is illustrated as including internal components in the fluid delivery assembly 16. Specifically, the system includes a monitor 24 for detecting an operational parameter characteristic of the injection procedure. For instance, the monitor 24 may be a pressure sensor that measures a partial vacuum established between the fluid delivery assembly 16 and the skin 18 of the patient 12 at the injection site 26. Similarly, the monitor 24 may be a pressure sensor that measures the reactive pressure exerted by the patient 12 against the fluid delivery assembly 16 when the fluid delivery assembly 16 is brought into contact with the skin 18 before an injection. Alternatively, the monitor 24 may include an electric lead for measuring conductance, or a receiver for measuring capacitance. In other embodiments, the monitor 24 may comprise an optical device for blood reading. In any case, the monitor 24 is provided to detect the desired operational parameter, whether it be pressure, conductance, capacitance, or blood composition.

As shown in FIG. 2, the monitor 24 is electronically connected to a timer 28. With this connection, the timer 28 is able to determine whether the operational parameter detected by the monitor 24 stays within a predetermined range during a first time interval "$\Delta t_1$" and during a second time interval "$\Delta t_2$". In FIG. 2, the monitor 24 and timer 28 are also connected to a controller 29. For purposes of the present invention, the controller 29 provides the ability to select the operational parameter, the predetermined range and the time intervals. Further, the controller 29 is connected to an actuator 30 which is connected to the fluid delivery assembly 16. With this design, the actuator 30 may initiate an injection procedure when activated by the controller 29.

It is to be appreciated that the functionality of the monitor 24, timer 28 and controller 29 should be considered in combination with each other as a unified control element. Specifically, it is important that such a control element detect an operational parameter and ascertain it to have a predetermined value, at specified times, for required time intervals. This can be accomplished in any of several different ways. For one, the monitor 24, timer 28 and controller 29 can interact with each other as a control element in a manner as described above. Also, in alternate embodiments for the present invention, the combined functions of the control element can be accomplished by devices such as: 1) software based microcontroller; 2) discrete electronic components such as transistors, resistors and capacitors; 3) discrete logic integrated circuits such as a comparator and timer; or 4) integrated logic circuit such as a programmable gate array.

Figure 3A:
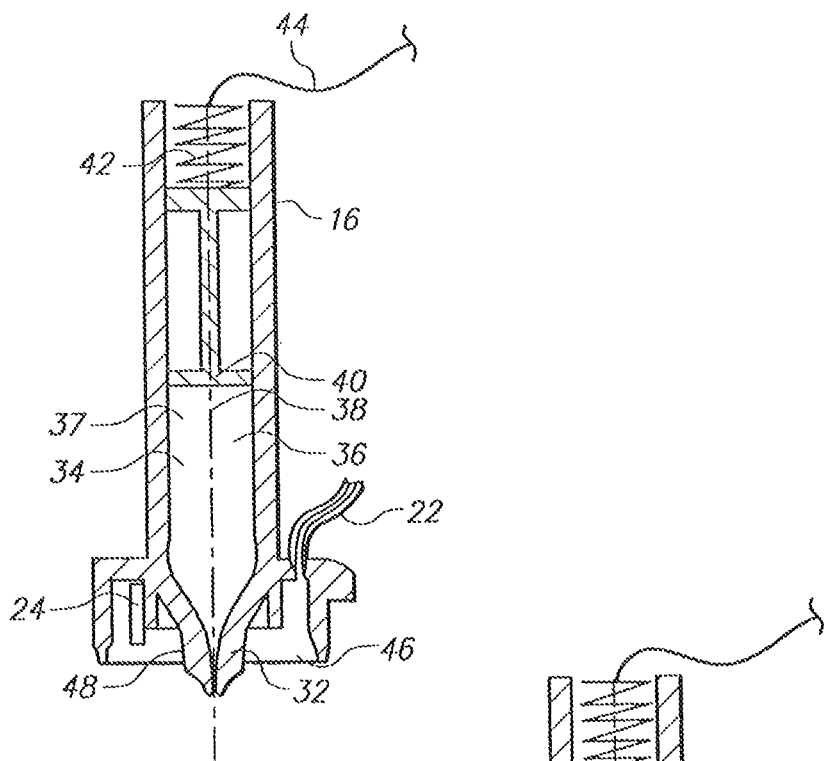
FIG. 3A is a cross sectional view of the fluid delivery assembly of FIG. 2 in accordance with the present invention.

Referring now to FIG. 3A, the construction of the fluid delivery assembly 16 is shown. In FIG. 3A, the fluid delivery assembly 16 includes an injector 32 for infusing a predetermined volume of medicament 34 into the patient 12. Structurally, the fluid delivery assembly 16 forms a fluid chamber 36 that holds a predetermined volume 37 of the fluid medicament 34 in fluid communication with the injector 32. As shown, the chamber 36 defines an axis 38. Further, a plunger 40 is positioned in the fluid chamber 36 for advancement along the chamber axis 36 through the chamber 36 to expel fluid medicament 34 through the injector 32. Also, a drive mechanism 42, such as a screw or spring, is provided for controlling movement of the plunger 40 in the chamber 36. As shown, a lead 44 connects the drive mechanism 42 to the actuator 30 (shown in FIG. 2).

Figure 3B:
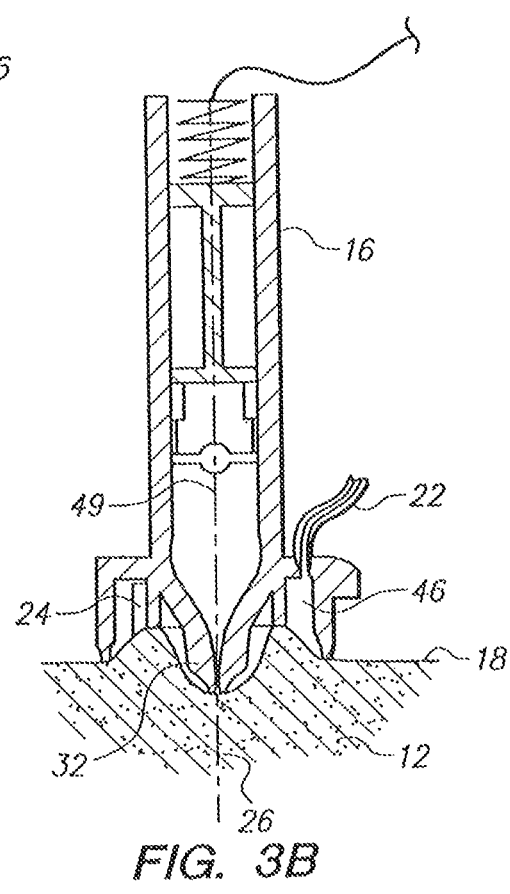
FIG. 3B is a cross sectional view of the fluid delivery assembly of FIG. 3A shown in engagement with the patient's skin and readied for an injection.

In the embodiment shown in FIG. 3A, the injector 32 is illustrated as a needleless type. Further, the fluid delivery assembly 16 forms a depression 46 around the external tip 48 of the injector 32. As shown, the vacuum line 22 is in communication with the depression 46 to provide a partial vacuum in the depression 46. Further, the monitor 24 is provided at the depression 46 to measure the pressure therein (or other operational parameter as desired). Referring now to FIG. 3B, the effect of a partial vacuum in the depression 46 is illustrated. In FIG. 3B, the fluid delivery assembly 16 has been positioned at the injection site 26 and the vacuum line 22 has created a partial vacuum to draw the patient's skin 18 into the depression 46. As shown, the monitor 24 is able to monitor the pressure in the depression 46. It is noted that FIG. 3B shows an alternate injector 32 which utilizes a needle 49.

Figure 4:
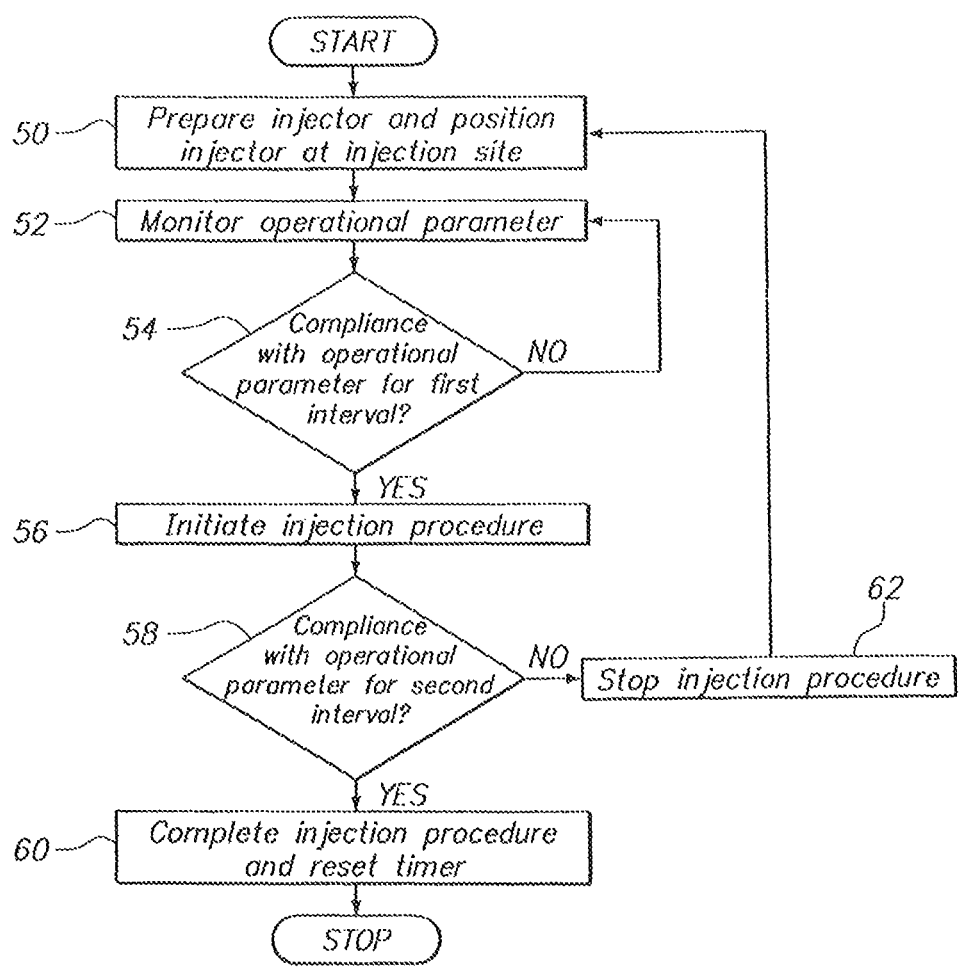
FIG. 4 is a schematic flow chart of the method of operation of the present invention.

Referring now to FIG. 4, the operation of the system 10 may be understood. As shown in FIG. 4, operation commences when an injector is prepared and the injector 32 is positioned at the injection site 26 (action block 50). For purposes of the present invention, this step may include programming the controller 29 with the predetermined volume 37 to be injected, the predetermined range for the operational parameter and the length of the first and second time intervals. Alternatively, each of these variables may be preset and unadjusted. For exemplary purposes, the predetermined volume may be 0.3 cubic centimeters, the predetermined range for partial vacuum pressure may be approximately 1 to 5 psia, the first time interval may be 2 seconds, and the second time interval is determined by the time necessary to infuse the required dose of fluid medicament.

After the injector 32 is positioned at the injection site 26, the operational parameter is detected by the monitor 24 (action block 52). As shown in inquiry block 54, the controller 29 determines whether the operational parameter has remained within the predetermined range for the first time interval. If it has not, the method returns to action block 52, or even action block 50 if the injector 32 needs to be repositioned at the injection site 26. If the operational parameter has remained within the predetermined range for the first time interval, the controller 29 prompts the actuator 30 to initiate the injection procedure (action block 56). During the injection, which lasts as long as the second time interval, the monitor 24 continues to detect the operational parameter as commenced in action block 52. As a result, in inquiry block 58, it is determined whether the operational parameter has remained within the predetermined range during the second time interval. As long as the operational parameter has been kept within the predetermined range, the injection may be completed at action block 60, and the operation may be concluded. If the operational parameter falls outside the predetermined range during the second time interval, the injection is stopped at action block 62. Thereafter, the injection procedure may be restarted at action block 50.

As can be seen from FIG. 4, the system 10 operates to prevent any premature injections, i.e., injections before an appropriate interface of the injector 32 with the skin or flesh has been established. As a result, patients can be confident that injections at difficult-to-reach areas will be accurate and properly administered. Further, the system 10 ensures continued engagement for infusion, thereby preventing injection interruptus.

While the particular Device and Method for the Automatic Initiation of an Injection as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for automatically initiating an injection procedure for injection of a fluid medicament into a patient which comprises:
    a fluid delivery assembly having an injector for infusing a predetermined volume of the medicament into the patient, the injector having an external tip with a depression formed around the external tip;
    a control element for setting a predetermined range of values of an operational parameter characteristic of the procedure;
    a monitor provided at the depression and electronically connected to the control element for detecting the operational parameter characteristic of the procedure in the depression when the injector is positioned at an injection site; and
    an actuator connected to the fluid delivery assembly, and responsive to the control element, for initiating the injection procedure by the fluid delivery assembly when the operational parameter characteristic is within the predetermined range of values.

2. A system as recited in claim 1 wherein the control element sets a time interval "$\Delta t_1$" and the system further comprises a timer electronically connected to the monitor for observing the operational parameter characteristic of the procedure and wherein the actuator is responsive to the timer for initiating the injection procedure by the fluid delivery assembly at the expiration of a time interval "$\Delta t_1$" within which the operational parameter characteristic stays within the predetermined range.

3. A system as recited in claim 1 further comprising a vacuum line in communication with the depression to provide a partial vacuum in the depression.

4. A system as recited in claim 3 wherein the injector is a needleless injector, and the operational parameter is a pressure value indicative of a partial vacuum established in the depression.

5. A system as recited in claim 1 wherein the injector is a needleless injector, and the operational parameter is a pressure value indicative of a partial vacuum established between the injector and an injection site on the patient.

6. A system as recited in claim 1 wherein the injector is a needle, and the operational parameter is a reaction pressure exerted by the patient against the fluid delivery assembly.

7. A system as recited in claim 1 wherein the operational parameter is selected from a group consisting of a conductance, a capacitance and an optical blood reading.

8. A system as recited in claim 1 wherein the fluid delivery assembly comprises:
    a fluid chamber for holding the fluid medicament, wherein the fluid chamber is in fluid communication with the injector; and
    a plunger positioned in the fluid chamber for advancement therethrough to expel fluid therefrom through the injector.

9. A system as recited in claim 8 further comprising a drive mechanism for advancing the plunger.

10. A system for automatically initiating and terminating an injection procedure for injection of a fluid medicament into a patient which comprises:
    a fluid delivery assembly having an injector for infusing a predetermined volume of the medicament into the patient, the injector having an external tip with a depression formed around the external tip;
    a control means for setting a predetermined range of values of an operational parameter characteristic of the procedure;
    a monitoring means for detecting the operational parameter characteristic of the procedure at the depression, the monitoring means electronically connected to the control means for detecting the operational parameter characteristic of the procedure in the depression when the injector is positioned at an injection site; and
    an actuating means for initiating the injection procedure by the fluid delivery assembly, the actuating means connected to the fluid delivery assembly, and responsive to the control means, to initiate the injection procedure by the fluid delivery assembly when the operational parameter characteristic is within the predetermined range of values.

11. A system as recited in claim 10 wherein the control means sets a time interval "$\Delta t_1$" and the system further comprises a timing means electronically connected to the monitoring means for observing the operational parameter characteristic of the procedure and wherein the actuating means is responsive to the timing means for initiating the injection procedure by the fluid delivery assembly at the expiration of a time interval "$\Delta t_1$" within which the operational parameter characteristic stays within the predetermined range.

12. A system as recited in claim 10 further comprising a vacuum line in communication with the depression to provide a partial vacuum in the depression.

13. A system as recited in claim 12 wherein the injector is a needleless injector, and the operational parameter is a pressure value indicative of a partial vacuum established in the depression.

14. A system as recited in claim 10 wherein the operational parameter is selected from a group consisting of a conductance, a capacitance and an optical blood reading.

15. A system as recited in claim 10 wherein the fluid delivery assembly further comprises:
- a fluid chamber for holding the fluid medicament, wherein the fluid chamber is in fluid communication with the injector;
- a plunger positioned in the fluid chamber for advancement therethrough to expel fluid therefrom through the injector; and
- a drive mechanism for advancing the plunger.

16. A method for automatically conducting an injection procedure for injection of a fluid medicament into a patient which comprises the steps of:
- providing a fluid delivery assembly having an injector for infusing a predetermined volume of the medicament into the patient, the injector having an external tip with a depression formed around the external tip;
- using a controller to set a predetermined range of values of an operational parameter characteristic of the procedure;
- monitoring the operational parameter characteristic of the procedure at the depression with a monitor that is connected to the controller to detect the operational parameter characteristic of the procedure in the depression when the injector is positioned at an injection site; and
- initiating the injection procedure by the fluid delivery assembly with an actuator connected to the controller when the operational parameter characteristic is within the predetermined range of values.

17. A method as recited in claim 16 further comprising the steps of:
- setting a time interval "$\Delta t_1$"; and
- electronically connecting a timer to the monitor for observing the operational parameter characteristic of the procedure, and wherein the actuator is responsive to the timer for initiating the injection procedure by the fluid delivery assembly at the expiration of a time interval "$\Delta t_1$" within which the operational parameter characteristic stays within the predetermined range.

18. A method as recited in claim 16 wherein the fluid delivery assembly further comprises a vacuum line in communication with the depression to provide a partial vacuum in the depression.

19. A method as recited in claim 18 wherein the operational parameter is a pressure value indicative of a partial vacuum established in the depression.

20. A method as recited in claim 16 wherein the fluid delivery assembly further comprises:
- a fluid chamber for holding the fluid medicament, wherein the fluid chamber is in fluid communication with the injector;
- a plunger positioned in the fluid chamber for advancement therethrough to expel fluid therefrom through the injector; and
- a drive mechanism for advancing the plunger.

* * * * *